(12) United States Patent
Li et al.

(10) Patent No.: US 6,376,508 B1
(45) Date of Patent: Apr. 23, 2002

(54) TREATMENTS FOR SPINAL MUSCULAR ATROPHY

(75) Inventors: Hung Li; Hsiu-Mei Hsieh-Li; Jan-Gowth Chang, all of Taipei (TW)

(73) Assignee: Academia Sinica, Taipei (TW)

(*) Notice: Subject to any disclaimer, the term of this patent is extended or adjusted under 35 U.S.C. 154(b) by 0 days.

(21) Appl. No.: 09/735,766

(22) Filed: Dec. 13, 2000

(51) Int. Cl.$^7$ .................. A61K 31/44; A61K 31/40; A61K 31/19; A61K 31/13
(52) U.S. Cl. .................. 514/300; 514/413; 514/557; 514/645
(58) Field of Search .................. 514/300, 413, 557, 645

(56) References Cited

PUBLICATIONS

Fricker, "Mouse model of spinal muscular atrophy," Drug Discovery Today 5:220–221(2000).
Frugier, et al., "Nuclear targeting defect of SMN lacking the C–terminus in a mouse model of spinal muscular atrophy," Human Molecular Genetics 9:849–858 (2000).
Gendron, et al., "Spinal muscular atrophy: molecular pathophysiology," Current Opinion in Neurology 12:137–142 (1999).
Gennarelli et al., "Survival motor neuron gene transcript analysis in muscles from spinal muscular atrophy patients," Biochemical and Biophysical Research 213:342–348 (1995).
Hsieh–Li, et al., "A mouse model for spinal muscular atrophy," Natural Genetics 24:66–70 (2000).
Jong, et al., "Analysis of the mRNA transcripts of the survival motor neuron (SMN) gene in the tissue of an SMA fetus and the peripheral blood mononuclear cells of normals, carriers and SMA patients," Journal of the Neurological Sciences 173:147–153 (2000).
Kijima, et al., "Trapoxin, an antitumor cyclic tetrapeptide, is an irreversible inhibitor of mammalian histone deacetylase*," Journal of Biological Chemistry 268:22429–22435 (1993).
Lorson, et al., "SMN oligomerization defect correlates with spinal muscular atrophy severity," Nature Genetics 19:63–66 (1998).
Lorson, et al., "An exonic enhancer is required for inclusion of an essential exon in the SMA–determining gene SMN," Human Molecular Genetics 9:259–265 (2000).
Monani, et al, "The human centromeric survival motor neuron gene (SMN2) rescues embryonic lethality in Smn— mice and results in a mouse with spinal muscular atrophy," Human Molecular Genetics 9:333–339 (2000).
Scharf, et al., "Identification of a candidate modifying gene for spinal muscular atrophy by comparative genomics," Nature Genetics 20 (1998).
Wong, et al., "The genetic and molecular mechanisms of motor neuron disease," Current Opinion in Neurobiology 8:791–799 (1998).
Yoshida, et al., "Potent and specific inhibition of mammalian histone deacetylase both in vivo and in vitro by trichostatin A*," Journal of Biological Chemistry 265:17174–17179 (1990).

*Primary Examiner*—William R. A. Jarvis
(74) *Attorney, Agent, or Firm*—Fish & Richardson, P.C.

(57) ABSTRACT

The invention features a method of modulating SMN exon 7 expression in a subject by administering a histone deacetylase inhibitor.

15 Claims, 3 Drawing Sheets

TREATMENTS FOR SPINAL MUSCULAR ATROPHY

BACKGROUND OF THE INVENTION

Spinal muscular atrophy (SMA) is an autosomal recessive neurodegenerative disease characterized by degeneration of spinal cord anterior horn cells, which lead to muscular paralysis with muscular atrophy. SMA patients are afflicted to varying degrees of severity and are therefore clinically categorized as type 1 (severe), 2 (intermediate), or 3 (mild), according to age of onset and rate of progression. The disorder is found in approximately 1 in 10,000 live births and has a carrier frequency of 1 in 50 (Zerres (1997) *J. Neurol. Sci.* 146:67–72). Type 1 patients have a life expectancy of 18 months or less, whereas type 3 patients can survive into adulthood.

All types of human spinal muscular atrophy are due to mutations in the SMN1 gene of the 5q13 locus on chromosome 5. In most individuals, there exists a second gene, SMN2, adjacent to SMN1. Both SMN1 and SMN2 encode SMN, a 294 amino acid RNA-binding protein (Lefebvre et al. (1995) *Cell* 80:155–165; Monani et al. (1999) *Hum. Mol. Genet.* 8:1177–1183). At the genomic level, only five nucleotides have been found that differentiate the SMN1 gene from the SMN2 gene. Furthermore, the two genes produce identical mRNAs, except for a silent nucleotide change in exon 7, namely, a C→T change six base pairs inside exon 7 in SMN2 as compared to SMN1. This mutation modulates the activity of an exon splicing enhancer (Lorson and Androphy (2000) *Hum. Mol. Genet.* 9:259–265). The result of this and the other nucleotide changes in the intronic and promoter regions is that most SMN2 transcripts lack exons 3, 5, or 7. In contrast, the mRNA transcribed from the SMN1 gene is generally a full-length mRNA with only a small fraction of its transcripts spliced to remove exon 3, 5, or 7 (Gennarelli et al. (1995) *Biochem. Biolphys. Res. Commun.* 213:342–348; Jong et al. (2000) *J. Neurol. Sci.* 173:147–153).

Furthermore, there is substantially less transcription of SMN2 than SMN1 in most individuals. As the severity of deletions of the SMN1 indicates, the low level of full-length SMN protein produced by SMN2 is insufficient to protect against spinal muscular atrophy disease (Lefebvre, supra; Coovert et al. (1997) *Hum. Mol. Genet.* 6:1205–1214).

There is no effective treatment to date for spinal muscular atrophy disease.

SUMMARY OF THE INVENTION

The invention is based on the discovery that different classes of compounds have been identified, using new methods, as being useful in the modulation of SMN exon 7 gene expression, and therefore as being useful in the treatment of SMA. It has also been discovered that cells harvested from SMA patients and transgenic animals having particular genotypes and phenotypes are useful in the new screening methods.

Accordingly, the invention features a method for modulating SMN gene expression in a subject. The method includes administering to the subject an amount of a histone deacetylase inhibitor sufficient to increase the expression level of SMN exon 7 in a cell of the subject, relative to a reference expression level of SMN exon 7.

Histone deacetylase inhibitors include butyrates (e.g., sodium butyrate, arginine butyrate, and butyric acid); trapoxin; and trichostatin A.

The reference level of SMN exon 7 can be the level in a cell of the subject prior to treatment, or a cell that has not been treated. The method can increase the expression level of SMN exon 7 by at least about 30%, 50%, 75%, 100%, 150%, 200%, 300%, 400%, 500% or greater. Alternatively, the increase can be measured by the ratio of transcripts containing exon 7 to those lacking exon 7. This ratio can be increased by at least about 30%, 50%, 75%, 100%, 150%, 200%, 300%, 400%, 500% or greater.

Also featured is a method of treating spinal muscular atrophy in a subject. The method includes administering to the subject a histone acetylase inhibitor in an amount sufficient to ameliorate a symptom of spinal muscular atrophy, e.g., a dosage described below. The subject can be a mammal, e.g., a human. A human subject can be homozygous for mutations in SMN1.

The subject can be a fetus that is treated in utero, e.g., by administering the histone acetylase inhibitor to the fetus directly or indirectly (e.g., via the mother).

As used herein, the term "transgene" refers to a nucleic acid sequence (e.g., encoding one or more human proteins), which is inserted by artifice into a cell. The transgene is integrated into a chromosomal genome. A transgenic sequence can be partly or entirely species-heterologous, i.e., the transgenic sequence, or a portion thereof, can be from a species which is different from the cell into which it is introduced. A transgenic sequence can be partly or entirely species-homologous, i.e., the transgenic sequence, or a portion thereof, can be from the same species as is the cell into which it is introduced. If a transgenic sequence is homologous (in the sequence sense or in the species-homologous sense) to an endogenous gene of the cell into which it is introduced, then the transgenic sequence has one or more of the following characteristics: it is designed for insertion, or is inserted, into the cell's genome in such a way as to alter the sequence of the genome of the cell into which it is inserted (e.g., it is inserted at a location which differs from that of the endogenous gene or its insertion results in a change in the sequence of the endogenous gene); it includes a mutation, e.g., a mutation which results in misexpression of the transgenic sequence; by virtue of its insertion, it can result in misexpression of the gene into which it is inserted, e.g., the insertion can result in a knockout of the gene into which it is inserted. A transgene can include one or more transcriptional regulatory sequences and any other nucleic acid sequences, such as introns, that may be necessary for a desired level or pattern of expression of a selected nucleic acid. A transgene can provide an antisense transcript or a sense transcript, e.g., a transcript encoding a protein.

As used herein, the term "transgenic cell" refers to a cell containing a transgene.

As used herein, a "transgenic animal" is a non-human animal in which one or more (e.g., all) of the cells of the animal contain a heterologous nucleic acid introduced by way of human intervention, such as by transgenic techniques known in the art. The transgene can be introduced into the cell directly, indirectly by introduction into a precursor of the cell, or by way of deliberate genetic manipulation, such as by microinjection, transformation, electroporation, lipofection, or infection with a recombinant virus. In one example, where the transgene is introduced indirectly, the transgene is introduced into a cultured cell, and the nucleus of the cultured cell or of a descendant of the cultured cell is microinjected into an enucleated oocyte to produce a nucleated oocyte which develops into an animal.

As used herein, a "disruption" in reference to an endogenous gene refers to any type of mutation that inactivates an endogenous gene, an exon thereof, or the amino acid sequence encoded by the endogenous gene or exon thereof. Consequently, the mutation can be a deletion of the disrupted gene or portion thereof, a mutation that causes inappropriate splicing (including abolishment of splicing), and/or and insertion into the disrupted gene or portion thereof.

In reference to subjects (e.g., animal models of SMA, e.g., a transgenic mouse model, and patients), a symptom of SMA is selected from: lethality before birth, before postnatal day 10, or before 4 weeks of age; decreased fetal movement; lethargy; loss or depression of muscular reflexes (e.g., areflexia, loss of gag reflex); hand tremors; peripheral neuropathies; large amplitude, prolonged, polyphasic discharges on active muscle contraction as detected by EMG (electromyography); myopathies; muscular weakness (e.g., weakness in the pelvic girdle, arms, facial muscles, instability of walking gait, paralysis of hind limbs, tongue fasciculation, and atrophy); myasthenia; hypertrophied muscle bundles (e.g., pseudohypertrophy of the calves); fat infiltration in muscle bundles; fibrosis in muscle bundles; necrosis in muscle bundles; muscular dystrophies; atrophy of muscle bundles (e.g., in tail, trunk, or limbs); decreased diameter of muscle fibers in the tail, trunk, or limbs; shorter and enlarged tails; chronic necrosis of the tail tip; subcutaneous edema; and reduced furry coat hair (see, e.g., Gendron and MacKenzie (1999) *Current Op. in Neurology* 12:137–142).

The skilled artisan can readily determine which of the list of symptoms would apply to a particular animal model. For example, a shortened tail is relevant only to those animals having a tail, and hand tremors are only relevant to those animals having a hand (e.g., a primate.). A symptom for type 1 spinal muscular atrophy in a mouse includes lethality before postnatal day 10, reduced furry coat hair, and a shortened and enlarged tail.

A used herein, the term "modulating" refers to a change in level, either an increase or a decrease. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is less than 0.05.

As used herein, "full-length SMN gene expression" or "expression level of SMN exon 7" refers to a scenario where an SMN gene is transcribed and the resulting transcripts contain exon 7 of an SMN gene. Specifically, it is of no consequence whether the exon 7-containing transcript is transcribed from the human SMN1 gene or from the human SMN2 gene. Transcripts containing SMN exon 7 are translated into the 294 amino acid SMN polypeptide. The amino acid sequence of the 294 amino acid SMN polypeptide is described in GenBank entry "GI:624186." The nucleic acid sequence of SMN exon 7 is the sequence contained between about nucleotides 868 and 921 of GenBank entry "GI:624185." The identify of the sixth base of exon 7 can be C (cytosine) if the transcript is derived from SMN1 or U (uracil) if the transcript is derived from SMN2. Exon 7 expression can be analyzed in cells in which SMN1 is deleted or mutated. Thus, the relevant SMN exon 7 sequence contains a uracil at position 873 while the remainder of the sequence is as recited from about nucleotides 868 to 921 of GenBank entry "GI:624185."

As used herein, a "histone deacetylase inhibitor" is a molecule which decreases the activity of a histone deacetylase enzyme in an in vitro assay. An assay for inhibition in vitro is described in Yoshida et al. ((1990) *J. Biol. Chem.* 265:17174–17179). A pure or semi-pure sample of eukaryotic histone deacetylase is obtained from FM3A tissue culture cells (e.g., available from Dr. Ayusawa, University of Tokyo, Japan). Cells are homogenized in buffer A (15 mM potassium phosphate, pH 7.5, 5% glycerol and 0.2 mM EDTA). The homogenate is centrifuged; then nuclei are pelleted by further centrifugation, and ruptured in buffer containing 1 M $(NH_4)_2SO_4$. The ruptured nuclei are sonicated and clarified by centrifugation. Histone deacetylase is precipitated from this fraction by increasing the $(NH_4)_2SO_4$ concentration to 3.5 M. The pellet is resuspended in buffer A, dialyzed against the same, loaded on a DEAE-cellulose column, and eluted with a linear NaCl gradient (0–0.6 M). The fraction eluting between 0.2 and 0.3 M NaCl and containing histone deacetylase is identified. Meanwhile, [$^3$H] acetyl-labeled histones are obtained from FM3A cells grow in the presence of 0.5 mCi/ml [$^3$H] acetate and 5 mM sodium butyrate. Histones are extracted from the cells using the method of Cousens et al. ((1979) *J. Biol. Chem.* 254:1716–1723). Assay tubes are prepared either containing the inhibitor molecule or containing a mock treatment, e.g., the solution and/or buffers in which the inhibitor is prepared. Then, 4 μl of [$^3$H] acetyllabeled histones and 96 μl of histone deacetylase are added. The tube is incubated at 37° C. for 10 minutes. The reaction is stopped with 10 μl of concentrated HCl. Released [$^3$H] acetic acid is extracted with 1 ml of ethyl acetate; 0.9 ml of the solvent layer is added to 5 ml of toluene or other acceptable scintillation solution and counted in a liquid scintillation counter. An inhibitor of histone deacetylase will decrease the amount of released [$^3$H] acetic acid relative to a control, e.g., by about 30%, 40%, 60%, 80%, 90% or greater.

Other features, objects, and advantages of the invention will be apparent from the following description and from the claims.

DETAILED DESCRIPTIOIN

Figure 1A:
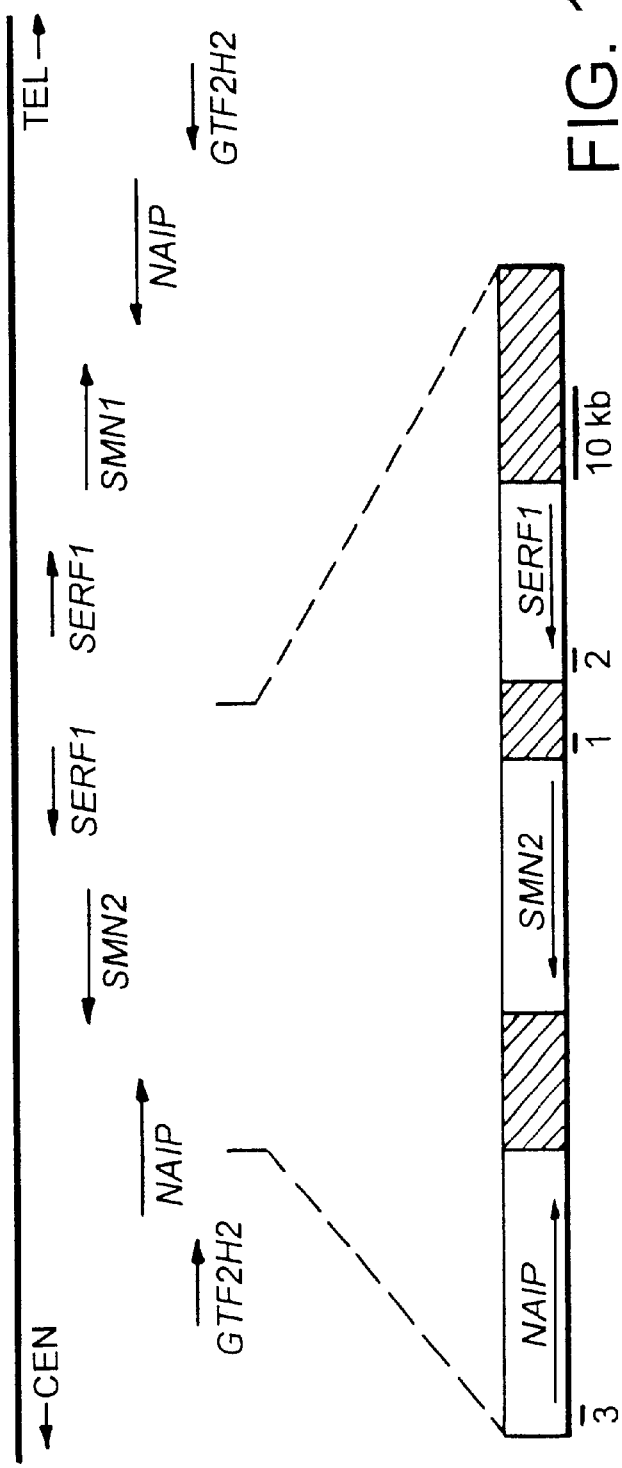
FIG. 1A is a schematic diagram of the human SMN locus used in a method of the invention.

The invention provides a treatment for spinal muscular atrophy. The treatment was identified using a screening method which incorporates two discoveries. First, an agent which increases expression of SMN gene exon 7 in transformed cell lines from SMA patients is indicative of an effective agent for ameliorating SMA symptoms. Second, the efficacy of an agent for treating SMA can be evaluated by administering to a mouse deleted for the murine SMN locus and bearing a human SMN2 transgene. This screening method has identified sodium butyrate as a candidate treatment for SMA.

Classes of Compounds Useful for Treating SMA

Sodium butyrate is used to ameliorate a symptom of SMA. Other butyrate, such as butyric acid and other butyrate salts (e.g., arginine butyrate) are also useful for treatment of SMA (see, e.g., U.S. Pat. No. 5,912,269).

Sodium butyrate is known to be an inhibitor of histone deacetylases. Other inhibitors of histone deacetylases include trapoxin (cyclo-(-L-phenylalanyl-L-phenylalanyl-D-pipecolinyl-L-2-amino-8-oxo-9,10-epoxy-decanoyl) and trichostatin A. Additional inhibitors can be identified, e.g., using the assay described in Yoshida et al. (1990) supra. A high-throughput screen of candidate or random compounds, e.g., in combination with the assay, can identify novel inhibitors. These agents can also be used to ameliorate a symptom of SMA. Moreover, these agents and other histone deacetylase inhibitors can be administered in combination.

The efficacy of derivatives of sodium butyrate can also be tested by the assays described herein. Possible derivatives are compounds similar to butyrates, but with different structures, chemical formulae, and, for example, different length alkyl chains. Such derivatives include: sodium propionate, and compounds with similar structures, e.g., sodium isovalerate, sodium 4-methyl valerate, methyl isobutyrate, and methyl butyrate.

The production and chemical properties of sodium butyrate are well known in the art. For example, butyric acid can be obtained from the fermentation of carbohydrates, or by reaction of n-propranol with carbon monoxide at 200 atm in the presence of $Ni(CO)_4$ and $NiI_2$.

Formulation.

A composition containing an effective amount of an inhibitor can be administered to a subject requiring treatment. The composition can be administered parenterally, intravenously, topically, orally, buccally, nasally, rectally, subcutaneously, intramuscularly, or intraperitoneally. In one implementation, the composition can be injected, e.g., into the cerebro-spinal fluid.

The composition for treatment is formulated to be compatible with the route of administration. The composition can be formulated as a tablet, capsule, solution, powder, inhalant, lotion, tincture, troche, suppository, or transdermal patch.

A solution for parenteral, intradermal, or subcutaneous administration can include: a sterile diluent such as water, saline, glycerin, fixed oils, polyethylene glycols, propylene glycol, or other synthetic solvents; an antibacterial agent such as benzyl alcohol or methyl parabens; an antioxidant such as ascorbic acid or sodium bisulfite; a chelating agent; a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Sterility can be insured by filter sterilization of the solution. Alternatively, the solution can be produced from components that were individually filter-sterilized. A filter-sterilized component can be vacuum dried or freeze dried to produce a sterile powder. Such a powder can be rehydrated prior to injection with a sterile carrier solution.

Oral compositions include tablets, capsules, troches, suspensions, and solutions. Such compositions can be fashioned with an inert diluent or an edible carrier. Capsules are made by combining an appropriate diluent with the compound and filling the capsule with the mixture. Common diluents are starches such as powdered cellulose, or sugars such as sucrose, fructose, or maniitol. Tablets are made by wet or dry granulation or by compression. In addition to the desired compound, compositions for tablets can include: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature. Biodegradable polymers such as poly-D,L-lactide-co-glycolide or polyglycolide, can be used as a matrix to delay the release of the composition (see e.g., U.S. Pat. Nos. 5,417,986, 4,675,381, and 4,450,150).

For administration by inhalation, the compounds are delivered in the form of an aerosol spray from pressured container or dispenser which contains a suitable propellant, e.g., a liquefied inert gas. Alternatively, the compounds can be delivered using a dry powder inhaler device, such as described in U.S. Pat. No. 4,907,583. These devices do not use liquefied propellants. Systemic administration can also be by transmucosal, e.g., with a nasal spray or suppository, or by transdermal means, e.g., as a salve, ointment, gel, or cream. Such modes of administration can use formulations containing detergents, bile salts, and fusidic acid derivatives to enhance absorption into the systemic circulation.

Dosage.

An appropriate dosage of the compounds for treatment must be determined. An effective amount of an inhibitor is the amount or dose which is required to ameliorate a spinal muscular atrophy symptom in a subject. Determination of the amount or dose required to treat an individual subject is routine to one skilled in the art, e.g., a physician, pharmacist, or researcher. First, the toxicity and therapeutic efficacy of the compound, e.g., sodium butyrate, is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios are greater than about 2, 5, 10, 50, or 100. Compounds, formulations, and methods of administration with high therapeutic indices can be determined, as such treatments have little toxicity at dosages which provide high efficacy. Compounds with toxic or undesirable side effects can be used, if means are available to deliver the compound to the affected tissue, i.e., the spinal motor neurons and brainstem neurons, while minimizing damage to unaffected tissue.

In formulating a dosage range for use in humans, the effective dose of an inhibitor can be estimated from studies with SMA-like cells and SMA-like transgenic mice. For example, therapeutically effective dosages in cell culture assays are about 5 ng/ml, 50 ng/ml, 500 ng/ml, 5 μg/ml, and 50 μg/ml of inhibitor. A dose can be formulated in an animal in order to achieve a circulating plasma concentration of inhibitor that falls in this range. An exemplary dose produces a plasma concentration which exceeds the $IC_{50}$ (i.e., the concentration of the test compound which achieves a half-maximal inhibition of a symptom) as determined in cell culture assays. The circulating plasma concentration can be determined, for example, by obtaining a blood sample, and by analyzing the sample with high performance liquid chromatography or mass spectroscopy.

Alternatively, the dose can be estimated from tests in an animal model, as described below. Alleviation of symptoms is observed when mice receive an inhibitor in their drinking water at doses of about 4 µg/day, 10 µg/day, 20 µg/day, 40 µg/day, 60 µg/day, and 80 µg/day. An appropriate dose for treating human patients is estimated to be approximately 0.4 mg kg$^{-1}$ day$^{-1}$, 1 mg kg$^{-1}$ days$^{-1}$, 2 mg kg$^{-1}$ days$^{-1}$, 4 mg kg$^{-1}$ day$^{-1}$, 60 mg kg$^{-1}$ days$^{-1}$, or approximately 80 mg kg$^{-1}$ day$^{-1}$. Depending on the method of administration, the appropriate dose can vary, e.g., from about 100 µg kg$^{-1}$ day$^{-1}$ to about 500 mg kg$^{-1}$ day$^{-1}$. The dose for a patient can be optimized while the patient is under care of a physician, pharmacist, or researcher. For example, a relatively low dose of sodium butyrate can be administered initially. The patient can be monitored for symptoms and for expression of SMN exon 7 as described herein. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

Monitoring.

The efficacy of a dose of inhibitor or any other treatment can be determined in a subject. For example, the subject can be monitored for clinical symptoms, e.g., muscular strength, muscle tone, muscular reflexes, gag reflex, ability to walk, and hand steadiness. An EMG (electromyograph) instrument can be used to assess active muscular contractions. For example, untreated subjects can exhibit large amplitude, prolonged, and polyphasic discharges. Subjects can also be directly monitored for affects on the level of SAfN exon 7 expression in cells. For example, blood or tissue samples can be obtained from the subject during treatment, and the level of SMN exon 7 expression in cells of the sample can be determined, e.g., by a nucleic acid or polypeptide detection method described herein. Alternatively, histopathologic analysis, including in situ nucleic acid hybridization, or in situ antibody staining, can be used to determine SMN exon 7 expression in a tissue sample, using the reagents and methods described herein.

Screening Reagents

Cell Lines.

Cell lines are derived from SMA patients. Such cells are termed "SMA cells" herein. The cells are isolated from a variety of sources and tissues. For example, the cells can be isolated from a blood sample or from a biopsy. The cell can be a stem cell, a fibroblast, or a lymphoid cell. The cells can be propagated in culture according to cell type and origin of the cells. The requisite growth factors can be provided in the media. For example, the media can be supplemented with fetal calf serum, a cocktail of purified factors, or an individual growth factor. The cells can be propagated without being immortalized. Alternatively, the cells can immortalized using a virus or a plasmid bearing an oncogene, or a transforming viral protein, e.g., papilloma E6 or E7 protein.

Procedures for isolating and maintaining lymphoid cells lines are well known in the art and can be found in suitable laboratory manuals, for example, Coligan et al. (1999) Sections 7.19.1–7.22.2, *Current Protocols in Immunology* John Wiley & Sons, Inc.

B cells can be immortalized with Epstein-Barr Virus (EBV). EBV virus is obtained from exponentially growing B95-8 cells (ATCC #CRL1612). The B95-8 cells are grown in a 37° C., 5% $CO_2$ humidified incubator for three days. The culture is then centrifuged at 300×g at 4° C. for ten minutes. The supernatant is filtered through a 0.45 pm filter, aliquoted, and stored at −130° C. A heparinized peripheral blood sample is obtained from an SMA patient. The sample is diluted 1:2 with PBS. 12 ml ofthe diluted sample is underlayed in a 50 ml conical centrifuge tube containing 12 ml of Ficoll-Hypaque. Ficoll-Hypaque can be purchased as Ficoll-Paque (Pharmacia) or made by dissolving 64.0 g ficoll (molecular weight 400,000), 99.0 g sodium diatrizoate, and 0.7 g sodium chloride in water such that the final volume is 1 L. The Ficoll gradient is centrifuged for 8 minutes at 1500×g at room temperature, or at 2500 rpm for 30 minutes. The buffy coat interface is removed, transferred to a new 50 ml conical tube, and washed twice with PBS. Washes can be performed by adding PBS, centrifuging for 15 minutes at 300×g, and discarding the supernatant. The cell pellet is then resuspended in HBSS (Hanks balanced salt solution), and washed twice. Finally, the cell pellet is resuspended in 2 ml to 5 ml of complete RPMI-10 media. $10^7$ cells in 2.5 ml of complete RPMI-10 are mixed with 2.5 ml of B95-8 culture supernatant containing EBV, incubated for 2 hours at 37° C., and then combined with 5 ml of RPMI-10 with 1 µg/ml cyclosporin A in a tissue culture flask. The flask is incubated for 3 weeks in a humidified 37° C., 5% $CO_2$ incubator. Subsequently, the cells are mixed and split into two new tissue culture flasks with fresh media. After 1 week, the cells can cryopreserved or used for long-term culture by splitting 1:3 in complete RPMI-10 weekly.

Protocols for transforming and transfecting tissue cultures are well known in the art; see for example Sambrook et al. (1989) *Molecular Cloning: A Laboratory Manual.* Cold Spring Harbor Laboratory Press, New York, and other suitable laboratory manuals. To insert a nucleic acid sequence into a cell, two particularly useful methods are electroporation and lipofection. For electroporation, cells can be collected and resuspended in PBS (phosphate-buffered saline) at a concentration of $2.10^6$–$5.10^6$ cells/ml. A 0.5 ml mixture of cells can be combined with 20–80 µg of linearized, isolated DNA and placed in a 0.4 cm electrode-gap cuvette (Biorad). A electroporator, e.g., Biorad Gene Pulser, is used to pulse the cells with a 330 volt pulse at 25 mAmp, 1000 µFarad, and infinite resistance. If the DNA construct contains a drug resistance marker, e.g., a neomycin resistance gene, cells can be grown in media with the drug, G418, present.

For lipofection, 2 µg of linearized, isolated DNA is mixed with LipfectAMINE™ (GibcoBRL) or another liposomal agent. The mixture is added to 2–$10^5$ cells in a 3.5 cm well of a tissue culture plate. After 48 hours, the cells are split, e.g., 1:1000, and, if a selectable marker is present on the introduced DNA, the cells are grown in the presence of the selecting drug. In one implementation, cells are lipofected with a DNA containing the human SMN2 gene, or a fragment thereof. Such DNA can contain additional features, such as a reporter gene fused to exon 7, and/or a selectable marker.

The cells can be grown in sufficient amount to screen an array of test compounds. Alternatively, cells can be used to assess the effectiveness of individual compounds as SMA treatments.

Mice.

The generation of transgenic animals is routine in the art. General methods for constructing transgenic mice can be found in Hogan et al. (1994) *Manipulating the Mouse Embryo*, Cold Spring Harbor Laboratory Press, New York.

A transgenic mouse bearing the human SMN2 gene is constructed. An isolated nucleic acid containing the human SMN2 gene can be obtained from a YAC, BAC or P1 clone spanning the SMN2 locus. For example, a BAC containing the human SMN2 locus can include about 35 kb, 50 kb, 80 kb, 100 kb, or preferably about 110 kb. Such a BAC can include genes flanking the human SMN2 gene, e.g., SERF1, and NAIP, or fragments thereof (see FIG. 1A). In one example, the human genomic DNA in the BAC is contiguous and identical to human DNA from the 5q13 region of human chromosome 5.

A variety of murine strains, such as FVB/N and C57BL/6, are suitable for use in the invention.

Mouse with a mutated murine SMN locus can be generated using gene targeting. A positive-negative selection vector, e.g., pGGKOV, can be used to target the locus. The invention features a mouse bearing a homozygous disruption of the murine SMN locus and the human SMN2 transgene. Such mice are generated by crossing a transgenic mouse containing the human SMN2 gene (hSMN2) with a mouse which is heterozygous for a disruption in the murine Sinn gene, i.e. $Smn^{+/-}$. Among the progeny of the cross is another mouse of this invention, the mouse being heterozygous for a disruption in the murine Smn gene, i.e. $Smn^{+/-}$ and bearing a transgene with hSMN2. Thus, the genotype of the mouse is $Smn^{+/-}$ hSMN2. Since mice lacking a SMN gene, whether endogenous or heterologous, are not viable, the $Smn^{+/-}$ hSMN2 mouse is useful as founder stock for the purposes of this invention.

The $Smn^{+/-}$ hSMN2 mouse can be bred using a F1 intercross, wherein siblings having both the $Smn^{+/-}$ hSMN2 genotype are mated to each other. Alternatively, the $Smn^{+/-}$ hSMN2 mouse can be mated to a $Smn^{+/-}$ mouse lacking hSMN2 The progeny of these crosses include mice which are homozygous for the murine SMN disruption, i.e. $Smn^{-/-}$, and which further contain the hSMN2 gene. These mice exhibit SMA symptoms and are used as an animal model for the human SMA, as described herein.

If these $Smn^{-/-}$ hSMN2 mice (also referred to as "SMA-like mice") are not severely affected, i.e. they show type 3 symptoms, they can be bred and used as founder stock to produce progeny of similar genotype, some of which can be more severely affected.

SMN Exon 7 Expression Analysis

The expression of SMN exon 7 is monitored, for example, in cells treated with a test compound, or in mock-treated cells. Generally, if the mean level of SMN exon 7 expression in cells treated with "test compound" is greater than the mean level of expression from a series of negative control experiments (e.g., mock-treated samples, or a set of inactive test compounds), and if the difference between the means is at least 2.5 times the standard deviation of the series of negative control experiments, then the "test compound" is considered a candidate for treatment of spinal muscular atrophy. Smaller differences in the means, however, are also useful in identifying potential compounds.

A number of techniques for monitoring SMN exon 7 expression are available. The production of transcripts containing exon 7 can be monitored directly. Polypeptides which include peptides encoded by Si4 N exon 7 can be detected, e.g., with an antibody. Additional methods are available.

Nucleic Acid Detection Assays

A variety of techniques are routinely practiced in the art to qualitatively and quantitatively assess the expression of an exon as an mRNA transcript. Generally, cells are cooled, and rapidly lysed, e.g., with a detergent or phenol. RNA is purified from the lysate, for example, by precipitation, or using a column, e.g., a oligo-dT column for binding poly-adenylated RNA, particularly mRNA. The isolated RNA is resuspended in solution, e.g., in water with 10 mM Tris-HCl pH 8.0, 1 mM EDTA. The water can be treated to inactivate or remove possible contaminating nucleases. The isolated cellular RNA is then probed for SMN exon 7, for example using a Northern blot or using reverse transcription and PCR (RT-PCR).

RNA isolation.

The isolation of total RNA from mammalian cells is routine in the art (e.g., see Sambrook et al. supra.). Cells are washed with PBS, then lysed with RNA extraction buffer (0.14 M NaCl, 1.5 mM $MgCl_2$, 10 mM Tris.HCl (pH 8.6), 0.5% Nonidet-P40 (NP-40), 1 mM dithiothreitol, Rnasin) and digested with proteinase K at 200 $\mu$g/ml. The lysate is sheered by repeated passage through a 21-gauge needle. The lysate is then extracted with phenol:chloroform (1:1), and centriftiged. The aqueous layer is then removed, mixed with 2.5 volumes with ice-cold ethanol for 1 hour at 4° C., then centrifuged. The RNA pellet is washed and resuspended for further analysis.

Northern Blotting.

Isolated RNA, about 2–10 $\mu$g/lane is electrophoresed on an garose gel, e.g., a 1.2% agarose gel containing 6.5% formamide and 20 mM MOPS (pH 7.0) 8 mM sodium acetate, 1 mM EDTA. The gel is electrophoresed at 120 V for approximately 2 hours or until adequate separation is achieved. The gel is then placed on a nitrocellulose filter and blotted overnight using 2×SSC (17.3 g sodium chloride, 8.82 g sodium citrate pH 7.0 per 1 L) and a wick made of Whatman 3MM paper. After blotting, the filter is rinsed and crosslinked with ultra-violet light. The filter is then mixed with a radiolabeled SMN exon 7 probe. The probe can be produced from isolated SMN exon 7 nucleic acid which is hybridized with random primers, and incubated with Klenow DNA polymerase, $^{32}$P-dATP, dCTP, dGTP, and dTTP. Alternatively, the probe can be produced by PCR using appropriate primers and $^{32}$P-dATP. The probe is then denatured and combined with the filter in hybridization buffer consisting of 18% formamide, 5×SSC, 5×Denhardt's Solution, 1% SDS, and 100 $\mu$g/ml denatured salmon sperm DNA. After 8–18 hours of incubation at 42° C., the hybridization buffer is removed, and the filter is washed two to three times at 65° C. with 2×SSC. The filter is then dried and autoradiographed. mRNAs containing exon 7 appear as bands on the autoradiogram.

RT-PCR.

Isolated RNA can be reverse transcribed using a primer, e.g., random primers, and MMLV reverse transcriptase (Promega). This reaction produces single-stranded cDNA which can be amplified by the polymerase chain reaction (PCR) using a thermostable DNA polymerase, and a pair of primers covering the SMN exon 7. One of the primers flanks exon 7 on the 5' end, the other flanks exon 7 on the 3' end. For example, one primer can anneal to coding sequences in exon 6, the other in exon 8. Alternatively, one or both of the primers can anneal to coding sequences in exon 7 itself. The amplification product is detected by agarose gel electrophoresis, ethidium staining, and illumination under a UV-light source. The amplification of exon 7 nucleic acid is indicative of exon 7 expression.

TaqMan assay.

A real-time PCR assay can be used to sensitively detect exon 7 transcripts using TaqMan technology and a Perkin- Elmer ABI7700 Sequence Detection system. After reverse transcription of a sample, the sample is prepared for a standard PCR reaction with oligonucleotides that will prime synthesis of fragment containing exon 7 nucleic acid or a fragment thereof. A third oligonucleotide, which is covalently linked to fluorescent dyes at its 3' and 5' ends, and which hybridizes to exon 7 is added. A fluorescent dye, such as 6-FAM, is used at the 5' end while a dye which quenches the 5' moiety is used at the 3' end, such as TAMRA. As a result of the quenching, prior to use, the fluorescent signal is low. However, if exon 7 sequences are present, the labeled oligonucleotide participates in intermolecular hybridization. The nucleolytic activity of Taq polymerase removes the 3' quenching dye and allows the remaining 5' dye to fluoresce. Thus, the PCR cycle when fluorescence is first detected is proportional to the concentration of template. The amount of total RNA can be internally controlled with a second oligonucleotide set which includes a probe oligonucleotide having a different fluorescence profile than the test probe and complementary to a control mRNA, such as actin.

Other molecular techniques can be used to detect the exon 7-containing SMN mRNA species. In one case, the ligase chain reaction is employed. In another case, hybridization to a microarray is monitored. The microarray, such as described below, can include additional nucleic acids to detect other transcripts whose splicing can be affected by treatment.

Antibody Assays

Alternatively, SMN exon 7 expression is monitored using an antibody specific to a polypeptide containing amino acids encoded by exon 7. The generation of specific antibodies is routine in the art.

For example, antibodies are generated to human SMN exon 7 as follows. Oligonucleotide primers are designed to amplify exon 7 nucleic acid such that the sequences are flanked by a restriction site that is compatible with a protein expression vector. Many protein expression vectors are commercially available for overproducing proteins in bacteria, insect cells, yeast, and mammalian cells. In one implementation, a vector containing the glutathione-S-transferase (GST) gene is used (Pharmacia). The vector includes unique restriction sites for in-frame fusion with GST. The PCR amplification product is cloned in-frame into the vector and transformed into an E. coli host cell. After protein synthesis is induced, the cells are harvested and lysed. The GST fusion to SMN exon 7 is purified on glutathione-coupled agarose beads, and eluted with free glutathione. Alternatively, the antigen can be removed from the column by cleavage with a specific protease, e.g., thrombin or factor Xa, provided that the requisite protease cleavage site was encoded in the linker between the GST gene and the inserted gene, i.e. SMN exon 7. If necessary, the antigen can be further purified, e.g., using ion-exchange chromatography, or by polyacrylamide gel electrophoresis. In the latter case, the antigen can be electroeluted from excised gel bands. The purified antigen is used to immunize rabbits, mice, hamsters, guinea pigs, or rats. An adjuvant can be used to enhance the immune response to the antigen. Adjuvants that can be used include Freund's (complete and incomplete), mineral gels, e.g., aluminum hydroxide, surface active substances, e.g., lysolecithin, pluronic polyols, polyanions, peptides, oil emulsions, keyhole limpet hemocyanin (KLH), and adjuvants compatible with use in humans, e.g., BCG (bacille Calmette-Guerin) and Corynebacterium parvum.

Monoclonals antibodies produced from a hybridoma cell are of utility as the hybridoma provides a homogenous population or antibodies. Hybridomas can be produced by fusing lymphoid cells from the spleen of immunized mice with an appropriate myeloma cell to produce a hybridoma (see, e.g., Kohler et al. (1975) Nature 256:495; Kohler et al., (1976) Eur. J. Immunol. 6:292; Hammerling et al., (1981) In Monoclonal Antibodies and T Cell Hybridomas, Elsevier, N.Y.; U.S. Pat. No. 4,376,110; Kosbor et al. (1983) Immunology Today 4:72; Cole et al., (1983) Proc Natl Acad Sci USA 80:2026; Cole et al., (1983) Monoclonal Antibodies and Cancer Therapy, Alan R. Liss, Inc., pp. 77–96). Monoclonal antibodies can be of any immunoglobulin class, e.g., IgG, IgM, IgE, IgA, or IgD, and of any subclass thereof. The hybridoma producing the monoclonal antibody can be cultivated in vitro or in vivo, e.g., in a mouse to obtain ascites fluid.

Antibodies are purified on beads coupled with the antigen and/or with Protein A-agarose. Antibodies can be tested for affinity and specificity by their ability to selectively recognize the antigen in a crude lysate by Western blot analysis or immunoprecipitation. Methods for Western blotting and immunoprecipitation are routine in the art and are described in Ausubel et al. (1994) Current Protocols in Molecular Biology, John Wiley & Sons, NY. Antibodies can be further modified to generate Fab fragments, $F(ab')_2$ fragments, humanized antibodies, chimeric antibodies, and single chain antibodies.

In an alternative example, peptides containing sequences from SIVN exon 7 are synthesized. The peptides are coupled to a carrier protein, e.g., KLH protein, and used to immunize animals as described above.

The SMN exon 7-specific antibodies are used to measure expression of exon 7 in SMA cells or in tissue samples and/or sections from patients and mice. Detection can be facilitated by coupling (i.e., covalently linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, $^{33}P$, $^{32}P$, and $^3H$.

To detect SMN exon 7 expression in cells, lysates can be prepared. Cells can be lysed in 25 mM Tris-HCl (pH 7.5), 50 mM potassium chloride, 1 mM dithiothreitol, 0.1% NP-40, 0.5 mM PMSF. Clarified lysates can either be analyzed by gel electrophoresis and Western blotting, or can be used to coat a plastic plate, and analyzed by ELISA (enzyme-linked substrate assay).

Reporter Gene Assays

In another implementation, a reporter gene is utilized to monitor the splicing of SMN2 exon 7. In a nucleic acid construction, the reporter gene is fused in frame to the SMN2 exon 7 in a region that itself is not required for splicing regulation. The construction also includes the remainder of the SMN2 gene such that the alternative splicing predilections of the SMN2 gene are recapitulated by the reporter. Alternatively, one skilled in the art can reduce the construction to smaller regions of the SMN2 gene such that the reduced region with the inserted reporter recapitulates the alternative splicing preferences of exon 7. Sodium butyrate is a useful positive controls for assessing the veracity of a reporter construct. The nucleic acid construction is transformed into SMA cells, e.g., by a transfection protocol or lipofection to generate SMA reporter cells.

In one implementation, the reporter gene is green fluorescent protein. In a second implementation, the reporter is β-galactosidase. In still other implementations, the reporter gene is alkaline phosphatase, β-lactamase, luciferase, or chloramphenicol acetyltransferase. The nucleic acid construction can be maintained on an episome or inserted into a chromosome, for example using targeted homologous recombination as described in Chappel, U.S. Pat. No. 5,272,071 and WO 91/06667.

In the implementation utilizing green fluorescent protein (GFP) or enhanced GFP (eGFP) (Clontech, Palo Alto, Calif.), the SMA reporter cells are grown in microtiter plates wherein each well is contacted with a unique agent to be tested. Following a desired treatment duration, e.g., 5 hours, 10 hours, 20 hours, 40 hours, or 80 hours, the microtiter plate is scanned under a microscope using UV lamp emitting light at 488 nm. A CCD camera and filters set for detecting light at 509 nm is used to monitor the fluorescence of GFP, the detected fluorescence being proportional to the amount of reporter produced as a consequence of altered splicing that favors exon 7 inclusion in the mRNA transcript.

In the implementation utilizing β-galactosidase, a substrate which produces a luminescent product in a reaction catalyzed by β-galactosidase is used. Again SMA reporter cells are grown in microtiter plates and contacted with compounds for testing. Following treatment, cells are lysed in the well using a detergent buffer and exposed to the substrate. Lysis and substrate addition is achieved in a single step by adding a buffer which contains a 1:40 dilution of Galacton-Star™ substrate (3-chloro-5-(4-methoxyspiro{1,2-dioxetane-3,2'-(4'chloro)-tricyclo-[3.3.1.1$^{3,7}$] decan}-4-yl)phenyl-B-D-galactopyranoside; Tropix, Inc., Cat.#GS 100), a 1:5 dilution of Sapphire II™ luminescence signal enhancer (Tropix, Inc., Cat.#LAX250), 0.03% sodium deoxycholic acid, 0.053% CTAB, 250 mM NaCl, 300 mM HEPES, pH 7.5). The cells are incubated in the mixture at room temperature for approximately 2 hours prior to quantitation. β-galactosidase activity is monitored by the chemiluminescence produced by the product of β-galactosidase hydrolysis of the Galacton-Star™ substrate. A microplate reader fitted with a sensor is used to quantitate the light signal. Standard software, for example, Spotfire Pro version 4.0 data analysis software, is utilized to analyze the results. The mean chemiluminescent signal for untreated cells is determined. Compounds which exhibit a signal at least 2.5 standard deviations above the mean are candidates for further analysis and testing. Similarly, for alkaline phosphatase, β-lactamase, and luciferase, substrates are available which are fluorescent when converted to product by enzyme.

Microarrays.

A large-scale or genome-wide analysis can identify additional transcripts which are either over- or under-expressed in SMA cells. For example, the splicing of other genes may be affected by a compound which affects SMN exon 7 splicing. Notably, the SMN protein itself is involved in mRNA splicing. Therefore, the production of full length SMN protein may impact the splicing of other genes. Alternatively, the compound may directly affect the splicing of other genes by the same mechanism as it affects SMN gene splicing.

In any event, any affected transcript can be identified by standard microarray experiments. A microarray can comprise a two-dimensional substrate having a plurality of addresses, with each address being positionally identifiable and having a unique nucleic acid sequence attached. cDNA can be prepared from untreated SMA cells and treated SMA cells. The cDNA is labeled, e.g., with a fluorescent probe, and hybridized to a microarray containing a large number of exonic sequences at addressable locations. The hybridization pattern of cDNA from treated and untreated cells is compared, and exons whose levels are altered by treatment are identified. For example, this experiment is performed with sodium butyrate as the treatment. Affected exons can be used as probes in subsequent drug screens. Alternatively, by identifying the gene containing the exon, reporter constructs can be designed to monitor the splicing of affected exons.

Screening a Test Compound

The invention provides methods (also referred to herein as "screening assays") for identifying modulators of SMN exon 7 expression. A "test compound" can be any chemical compound, for example, a small organic molecule, a carbohydrate, a lipid, an amino acid, a polypeptide, a nucleoside, a nucleic acid, or a peptide nucleic acid. The test compound or compounds can be naturally occurring, synthetic, or both. A test compound can be the only substance assayed by the method described herein. Alternatively, a collection of test compounds can be assayed either consecutively or concurrently by the methods described herein.

Such modulators can include macromolecules and small molecules, such as molecules having a formula weight of less than about 10,000 grams per mole, less than 5,000 grams per mole, less than 1,000 grams per mole, or less than about 500 grams per mole. Macromolecules include, but are not limited to polypeptides, e.g., proteins, protein complexes, and glycoproteins, nucleic acids, e.g., DNA, RNA and PNA. (peptide nucleic acid). Small molecules include, but are not limited to, peptides, peptidomimetics (e.g., peptoids), amino acids, amino acid analogs, polynucleotides, polynucleotide analogs, nucleotides, nucleotide analogs, organic or inorganic compounds e.g., including heteroorganic and organometallic compounds). Modulators can be identified using a drug screen. Molecules can be screened individually or in parallel. Compounds can be obtained from a commercial chemical supplier, e.g., Sigma-Aldrich Corp., St. Louis, Mo.

A large scale example of the latter is a high throughput drug screen. A high-throughput method can be used to screen large libraries of chemicals. Such libraries of candidate compounds can be generated or purchased e.g., from Chembridge Corp., San Diego, Calif. Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. Alternatively, prior experimentation and anecdotal evidence, can suggest a class or category of compounds of enhanced potential. A library can be designed and synthesized to cover such a class of chemicals.

High Throughput Screening

Transformed cells from SMA patients can be used for high throughput drug screening. For example, the cells can be grown in small microtiter plates, e.g., 6-well, 32-well, 64-well, 96-well, 384-well plates. High density microtiter plates can be fashioned from a polymer, e.g., polydimethylsiloxane, (e.g., Sylgard 384 from Dow-Corning) and an acrylic mold. The mold contains wells for the growth of cells into which compounds can be dispensed. For example, a mold can contain 1536 wells with a 2 $\mu$l capacity, or 6144 wells with a 250 nl capacity. The transformed SMA cells are grown in each well. Then a plurality of candidate compounds can be screened. Alternatively, a library, as described above, can be screened. The library can be provided in a format that is amenable for robotic manipulation, e.g., in microtiter plates. Compounds can be added to SMA cells in microtiter plates. Following compound addition, cells are incubated for a specific time. Then, the expression level of SMN exon 7 is monitored. A high through put screen is further facilitated by the use of a reporter gene to monitor the splicing of SMN2 exon 7 as described above.

The compounds can also be pooled, and the pools tested. Positive pools are split for subsequent analysis. Regardless of the method, compounds which increase the expression level of SMN exon 7 are considered "candidate" compounds or drugs. Candidate compounds are retested on SMA cells as described above. They are also tested on SMA-like mice, as described herein. Candidate compounds that are positive in a retest are considered "lead" compounds.

Optimization of a Compound

Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above described assays can be delineated by examination of structure-activity relationships (SAR) as is commonly practiced in the art. A person of ordinary skill in pharmaceutical chemistry could modify moieties on a lead compound and measure the effects of the modification on the efficacy of the compound to thereby produce derivatives with increased potency. For an example, see Nagarajan et al. (1988) *J. Antibiot.* 41:1430–8. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software is commercially available (e.g., Molecular Simulations, Inc.)

Without further elaboration, it is believed that the above description allows the skilled artisan to practice the present invention. The following examples are therefore to be construed as merely illustrative and not limitative of the remainder of the disclosure in any way whatsoever. All of the publications cited herein are hereby incorporated by reference in their entirety.

EXAMPLES

1. Drug Screens for SMN Exon 7 Expression in Cell Lines

To identify drugs for treating spinal muscular atrophy, EBV transformed lymphoid cell lines of all three types of SMA patients were developed and assayed as follows.
Transformed Cell Lines.

Lymphoid cells were isolated from SMA patients with different degrees of severity. Whole blood was drawn from the patients, heparinized, then diluted 1:1 with PBS (phosphate buffered saline). The diluted sample was layered on a Ficoll-Hypaque gradient, and centrifuge at 2500 rpm for 30 minutes at room temperature. The buffy coat was collected from the centrifuged sample, washed twice with 5 ml PBS, collected, and resuspended in 5 ml RPMI medium, 0.5 ml Epstein-Barr virus (EBV stock), 50 $\mu$l PHA, and 50 $\mu$l of cyclosporine (0.2 mg/ml). The virus-treated sample was mixed well and transferred into a T-flask for incubation at 37° C. in a 5% $CO_2$ incubator for 3 weeks.

Several drugs were screened for their ability to increase exon 7 expression from the SMN2 gene. Two types of screens are described. One utilizes RT-PCR analysis, and the other utilizes an antibody specific to SMN exon 7 epitopes.
RT-PCR Analysis.

Total RNA from treated lymphoid cells and untreated controls was reverse transcribed using the random primer 5'-$TN_{10}$-3' and MMLV reverse transcriptase (Promega). The resulting single-stranded cDNA was amplified by the polymerase chain reaction (PCR) using one of three pairs of primers covering the entire SMN coding region. The primer pair for amplification of the nucleic acid fragment from the 5' untranslated region to exon 4 was: 5'-CGCTGCGCATCCGCGGGTTTGCTATG GC-3' (forward primer, P1, SEQ ID NO:1) and, 5'-TCCCAGTCTTGGCCCTGGCAT-3' (reverse primer, P2, SEQ ID NO:2). The primer pair for amplification of the nucleic acid fragment from exon 4 to exon 6 was: 5'-AACATCAAGCCCAAATCTGC-3' (forward primer, P3, SEQ ID NO:3), and 5'-GCCAGTATGATAGCCACTCATGTACCATG-3' (reverse primer, P4, SEQ ID NO:4). The primer pair for amplification of the nucleic acid fragment from exon 6 to exon 8 was: 5'-CTCCCATATGTCCAGATTCTCTTGATGA TGC-3' (forward primer, P5, SEQ ID NO:5), and 5'-ACTGCCTCACCACCGTGCTGG-3' (reverse primer, P6, SEQ ID NO:6). Primers P1 and P6 were used to amplify the full length SMN cDNA. PCR amplification products were analyzed on agarose gels. The production of a 419 basepair band from primers P5 and P6 was indicative of increased exon 7 expression, whereas a 365 basepair band was indicative of a splice pattern which excludes exon 7.
Western-blot Analysis.

Rabbits were immunized with synthetic peptides containing either human SMN amino acids 279–288 from exon 7 or amino acids 72–84 from exon 2. Specific antibodies (H7 and H2 batches) were purified from rabbit crude sera with an EAH-sepharose 4B column (Pharmacia) according to the manufacturer's instructions.

Protein samples, prepared from treated and untreated SMA lymphoid cells, were loaded on a 5% polyacrylamide stacking gel above a 12% separating gel, and the gel was run with a discontinuous buffer using Laemmli's method. After electrophoresis, proteins were transferred electrophoretically to polyvinyl difluoride membranes (Millipore Corp., Marlborough, Mass., USA). After the transfer, the membranes were blocked in TBST (50 mM Tris-HCl, pH 7.5, 150 mM NaCl, 0.05% Tween 20) containing 4% BSA (bovine serum albumin) for 2 hours at room temperature. Blots were incubated with a 1:800 dilution of anti-SMN exon 2 (H2) or anti-SMN exon 7 (H7) antibody in TBST for 2 hours at room temperature. The blots were washed for three 20-minute periods in TBST and then incubated with a 1:32,000 dilution of an anti-rabbit IgG alkaline phosphatase conjugate (Sigma) in TBST for 1 hour at room temperature. The secondary antibody was detected with a 1.5% solution of 5-bromo-4-chloro-3-indoyl phosphate and 3% nitro blue tetrazolium in a developing buffer (100 mM NaCl, 5 mM $MgCl_2$, 100 mM Tris.HCl, pH 9.5).

2. Effects of Sodium Butyrate on SMA-like Cell Lines

One of the compounds, sodium butyrate, changed the expression pattern of exon 7 of the SMN2 gene. The amount of exon 7-containing SMN mRNA increased in the lymphoid cells cultured with 5 ng/ml to 50 µg/ml of sodium butyrate, with the greatest increase being 4 hours after addition of the drug. Moreover, lymphoid cells from all three types of SMA patients showed increased levels of full-length SMN transcript. Since at least one of these cell types contains a deletion of the SMN1 gene, the increase in SMN exon 7 was necessarily due to alterations in SMN2 splicing.

The RT-PCR method described above was used to determine the alternative splice pattern of the SMN2 gene. In untreated cells, SMN2 was normally spliced to remove exon 7. However, after sodium butyrate treatment, the splicing of SMN2 transcripts was changed to include exon 7 as in the splicing of SMN1 transcripts. Treatment also resulted in an increase in the amount of full-length SMN mRNA transcript, relative to the untreated control.

In addition, sodium butyrate treatment resulted in an increase in the levels of exon 7-containing SMN protein. Lymphoid cell lines established from different types of SMA patients were treated with varying amounts of sodium butyrate and compared to untreated controls. Western blot analysis using the H2 and H7 antibodies produced as described above indicated that sodium butyrate increase the amount of intact SMN protein. This increase in intact SMN protein was evident in both cytosolic and nuclear fractions after 4 hours stimulation with 0.5 ng/ml to 5 µg/ml of sodium butyrate.

3. Generation of Mice with SMA-like Symptoms

Figure 1B:
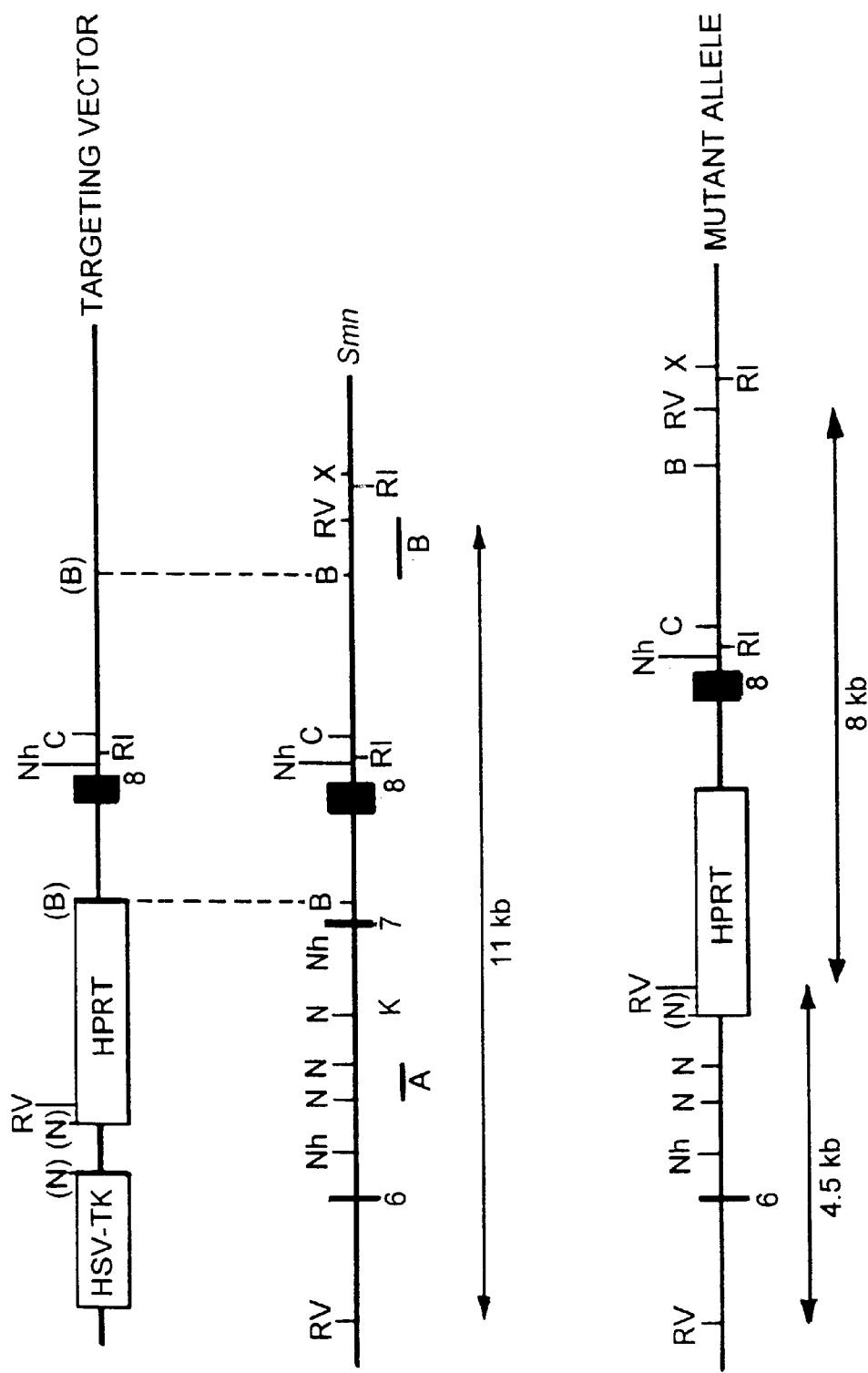
FIG. 1B is a schematic diagram of the mouse SMN locus and an insertion of human sequences into the mouse locus in a method of the invention.
Figure 2:
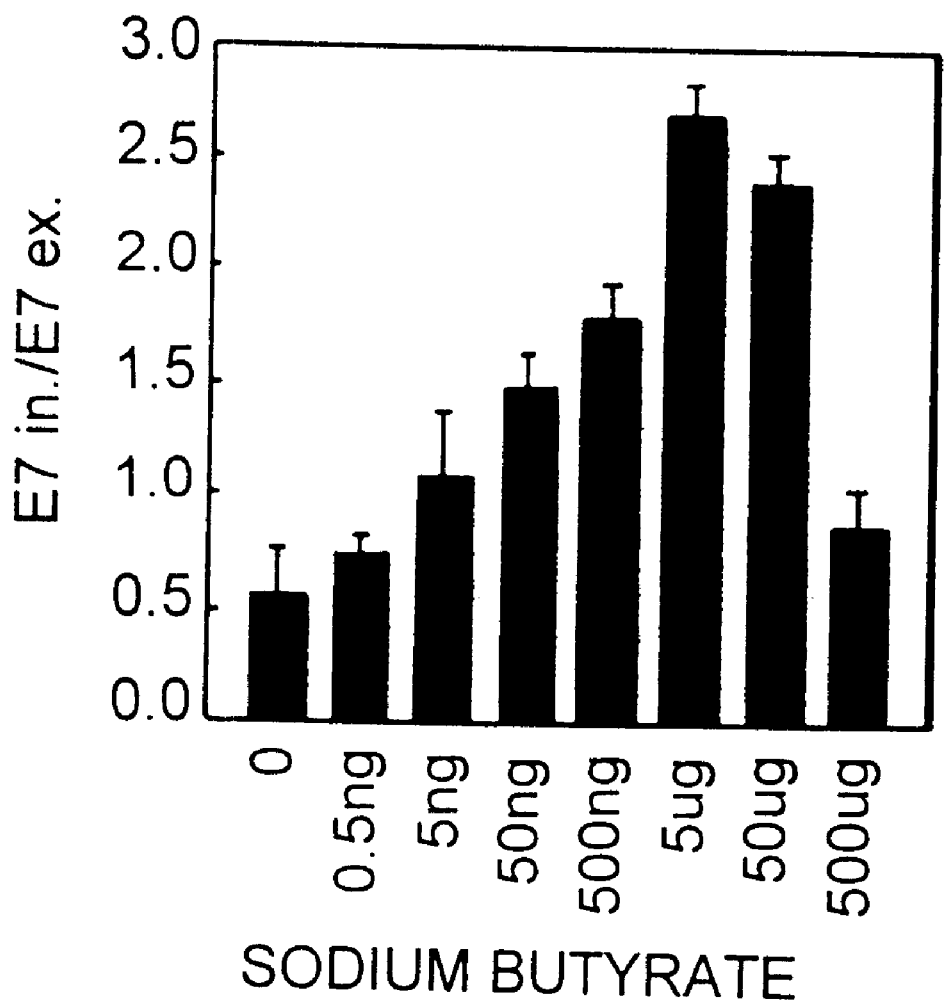
FIG. 2 is a bar graph depicting the ratio of SMN transcripts having exon 7 to those lacking exon 7 (E7 in./E7 ex.) in transformed lymphocytes treated with various concentrations of sodium butyrate (indicated amounts are per ml).

Transgenic Mice. A mouse containing a mutation in the murine SMN gene was generated with the plasmid pGGKOV-SMN (Hsieh-Li et al. (2000) *Nature Gen.* 24:66–70). This plasmid contains a 1.6 kb deletion of the murine SMN locus. The deletion removes exon 7. To generate pGGKOV-Smn, the 4.6 kb BamHI fragment and the 0.6 kb NdeI fragment of the mouse genomic clone MSG24-4, which spans the SMN cDNA exons 2 to 8, were cloned into the BamHI and ClaI sites, respectively, of the pGKKOV vector (see FIG. 1B). For details of the pGGKOV vector and methods for its use see Li et al. (1996) *EMBO J.* 115:714–724.

pGGKOV-Smn was linearized with NotI and electroporated into E14TG2a embryonic stem cells. Cells were selected for integration of the HPRT gene and against integration of HSV-thymidine kinase, in order to obtain homologous recombinants which disrupt the Smn exon 7 as described (Li et al., supra). Cells were injected into C57BL/6 blastocysts using standard procedures (Hogan et al., supra). The resulting mice were bred and individuals heterozygous for the Smn gene disruption were identified by genotyping.

hSMN2 transgenic mice were generated as follows. The 115 kb insert of the hSMN2 BAC clone 7C was excised with NotI, purified on an agarose gel, and electroeluted from the gel. The 115 kb insert includes, from the centromeric side to the telomeric side, the NAIP gene, the SMN2 gene, the SERF1 gene, and 35 kb of nucleic acid telomeric to the SERFI gene (see FIG. 1A). The DNA was then diluted to 2 ng/µl and injected into FVB/N male mice pronuclei as described (Hogan et al., supra).

To generate hSMN2 $Smn^{+/-}$ mice, a mouse heterozygous for the murine Smn disruption was crossed to a mouse containing the hSMN2 transgene. Progeny were genotyped to identify hSMN2 $Smn^{+/-}$ mice.

To generate hSMN2 $Smn^{-/-}$ mice, hSMN2 $Smn^{+/-}$ mice were crossed to $Smn^{+/-}$ mice. Progeny lacking the murine SMN locus were identified by genotyping. The presence of the hSMN2 transgene was also confirmed. Such mice, having the hSMN2 $Smn^{-/-}$ genotype, exhibit a range of SMA symptoms and are referred to as "SMA-like" mice.

Mice with the most severe pathology (type 1) did not develop furry hair and died before postnatal day 10. Mice with intermediate severity (type 2) were inactive, and died at approximately 2 to 4 weeks. These mice frequently developed chronic necrosis of the tail tip, muscular atrophy, subcutaneous edema in hindlimbs, and paralysis of hindlimbs. Type 3 mice survived and bred normally. The mild symptoms of these mice include short but enlarged tails.

4. Treatment of types 2 and 3 SMA-like Mice with Sodium Butyrate

The effect of sodium butyrate on the symptoms of SMA-like mice were investigated. Sodium butyrate was administered to ten SMA-like mice with type 2 symptoms and ten SMA-like mice with type 3 symptoms. These mice were identified at birth by genotype and phenotype. Thereafter, their drinking water was supplemented with a 0.8 µg/ml or an 8 µg/ml solution of sodium butyrate. The drinking water was available ad libitum. The amount of sodium butyrate taken by SMA-like mice was estimated to be approximate 4–80 µg/day. The survival time of sodium butyrate-treated type 2 SMA-like mice was longer, about 4 to 5 days longer on average, than untreated mice.

The effect of sodium butyrate administration on the tail phenotype of SMA-like mice was also monitored. The tails of untreated types 2 and 3 SMA-like mice have decreased diameter of muscle fibers, atrophy of muscle bundles, group atrophy and subcutaneous edema (Hsieh-Li et al. (2000) supra). However, sodium butyrate treatment restored the tail phenotype of type 3 SMA-like mice close to wild-type in experiments monitoring greater than 200 hundred type 3 SMA-like mice. The tail of a treated mouse was about 5 cm long on average, whereas the tail of an untreated mouse was about 1 cm long. Remarkably, the average length of the tail of treated mice, 5 cm, is close to the average length for wild-type mice, 6 cm. The frequency of chronic necrosis originating at the tip of the tail was markedly reduced to 2% in sodium butyrate-treated SMA-like mice in comparison to 50% for untreated SMA-like mice. Similarly, the tail of treated SMA-like mice had fewer atrophied muscle bundles, less group atrophy, and reduced subcutaneous edema relative to untreated SMA-like mice. The results of western blot analysis and immunohistochemical studies demonstrated that, in sodium butyrate-treated SMA-like mice, exon 7-containing SMN protein levels were elevated in multiple tissues, including spinal cord motor neurons.

There was a very strong correlation between the function of a compound in the above-described assay of transformed lymphoid cells from SMA patients and its affect on the neurological phenotype of SMA-like diseased animals.

5. In Utero Treatment of SMA-like Mice

To evaluate the therapeutic effect of sodium butyrate for severely affected SMA mice, the test compound was administered to pregnant mice from an hSMN2 Smn$^{+/-}$ intercross. The number mice born with SMA-like phenotypes were counted and classified according to type. In one case, 4–8 µg/day sodium butyrate was administered to pregnant mice from a hSMN2 Smn$^{+/-}$ intercross ad libitum in their drinking water beginning from 15 day post-coitum until parturition (Table 1).

TABLE 1

|  | Sodium Butyrate Treated Mothers | Untreated Control Mothers |
| --- | --- | --- |
| Litters | 32 | 46 |
| Total pups | 294 | 364 |
| Type 1 | 21 (7%) | 35 (10%) |
| Type 2 | 22 (7%) | 17 (5%) |
| Type 3 | 48 (16%) | 38 (10%) |

The number of severely affected progeny (i.e., with Type I symptoms) was reduced when the mothers were treated with sodium butyrate relative to the progeny from untreated mothers. Of the progeny, only 7% of the progeny of sodium butyrate-treated mothers had type 1 symptoms in comparison to 10% of progeny from untreated mothers. These results demonstrate that sodium butyrate treatment at day 15 of pregnant intercross mothers ameliorated the clinical symptoms in progeny mice from the severe SMA group (type 1) to milder type SMA groups (types 2 and 3). The statistical p value was less than 0.05.

In an additional experiment using a higher dose, 40–80 µg/day of sodium butyrate, again the progeny from treated mothers had milder symptoms than the progeny from untreated mothers.

Other embodiments are within the following claims.

What is claimed is:

1. A method for modulating SMN gene expression in a subject, the method comprising administering to the subject an amount of a histone deacetylase inhibitor sufficient to increase the expression level of SMN exon 7 in a cell of the subject, relative to a reference expression level of SMN exon 7.

2. The method of claim 1 wherein the histone deacetylase inhibitor is a butyrate, trapoxin, or trichostatin A.

3. The method of claim 2 wherein the histone deacetylase inhibitor is sodium butyrate.

4. The method of claim 1 wherein the ratio of SMN transcripts having exon 7 to those lacking exon 7 is increased by at least 50%.

5. The method of claim 4 wherein the ratio of SMN transcripts having exon 7 to those lacking exon 7 is increased by at least 100%.

6. A method of treating spinal muscular atrophy in a subject, the method comprising administering to the subject a histone acetylase inhibitor in an amount sufficient to ameliorate a symptom of spinal muscular atrophy.

7. The method of claim 6 wherein the histone deacetylase inhibitor is a butyrate, trapoxin, or trichostatin A.

8. The method of claim 7, wherein the histone deacetylase inhibitor is a butyrate.

9. The method of claim 8, wherein the histone deacetylase inhibitor is sodium butyrate.

10. The method of claim 6, wherein the subject is human.

11. The method of claim 10, wherein the subject is homozygous for mutations in SMN1.

12. The method of claim 11, wherein the subject is a fetus, and the histone acetylase inhibitor is administered to the subject in utero.

13. The method of claim 6, wherein the symptom is muscular paralysis.

14. The method of claim 6, wherein the symptom is muscular atrophy.

15. The method of claim 6, wherein the symptom is decreased expression of SMN exon 7 in a cell of the subject.

* * * * *

UNITED STATES PATENT AND TRADEMARK OFFICE
CERTIFICATE OF CORRECTION

PATENT NO. : 6,376,508 B1
APPLICATION NO. : 09/735766
DATED : April 23, 2002
INVENTOR(S) : Hung Li, Hsiu-Mei Hsieh-Li and Jan-Gowth Chang It is certified that error appears in the above-identified patent and that said Letters Patent is hereby corrected as shown below:

Column 20
Line 16, delete "histone acetylase inhibitor", insert -- histone deacetylase inhibitor --

Signed and Sealed this

Thirtieth Day of January, 2007

JON W. DUDAS
*Director of the United States Patent and Trademark Office*